US00PP10210P

United States Patent [19]

Osiecki

[11] Patent Number: Plant 10,210

[45] Date of Patent: Jan. 20, 1998

[54] ANTHURIUM PLANT "A2"

[75] Inventor: Marian W. Osiecki, Marianna, Fla.

[73] Assignee: Oglesby Plant Laboratories, Inc., Altha, Fla.

[21] Appl. No.: 753,874

[22] Filed: Dec. 2, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz

[57] ABSTRACT

A new variety of Anthurium is provided. It is a dwarf plant, suitable for production in 7.5 cm to 15 cm pots. It can be produced in a 7.5 cm container within 7–8 months from planting a single tissue culture produced microcutting. 'A2' has vigorous growth; early branching; abundant, year-round and extremely early natural flowering. Pink spathes of a good quality from the onset of flowering, large in relation to the plant, are held above foliage on straight, thick, strong, peduncles. After maturity spathes gradually become green and continue their attractiveness on the plant.

2 Drawing Sheets

This invention relates to a new and distinct Anthurium cultivar characterized by the following combination of repeatedly observed traits:

1. Dwarf size,
2. vigorous growth,
3. early branching,
4. abundant, year-round and exceptionally early flowering,
5. inflorescence of good quality from the onset of flowering,
6. straight, thick, strong peduncles,
7. spathes large in relation to plant and held above foliage,
8. spathes pink, gradually changing to green, with long ornamental value and primarily selected for those characteristics being so selected from the progeny of the cross stated below being grown near Altha, Fla. in a cultivated area.

ORIGIN AND ASEXUAL REPRODUCTION

The new cultivar is a product of a planned breeding program carried out at Oglesby Plant Laboratories, Inc. Near Altha, Fla. The female parent was a selected clone of Anthurium 'Julia' designated "J90302" and the male parent was a selected *Anthurium andreanum* designated "AR891". The cross was made in 1991 and the seedling was selected in 1992 and it has been reproduced by tissue culture in the vicinity of Altha, Fla. since 1993 with the characteristics stated, found to be maintained through successive generations.

This new cultivar has been identified as Anthurium 'A2'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'A2' was approximately 12 months from planting a single tissue cultured microcutting and was grown in a 10 cm pot.

In the the photographs:

DETAILED DESCRIPTION OF THE NEW CULTIVAR

Figure 1:
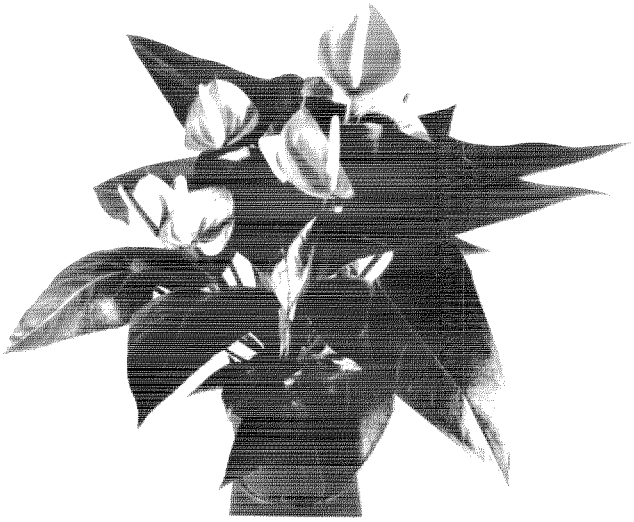
FIG. 1 depicts the whole plant.
Figure 2:
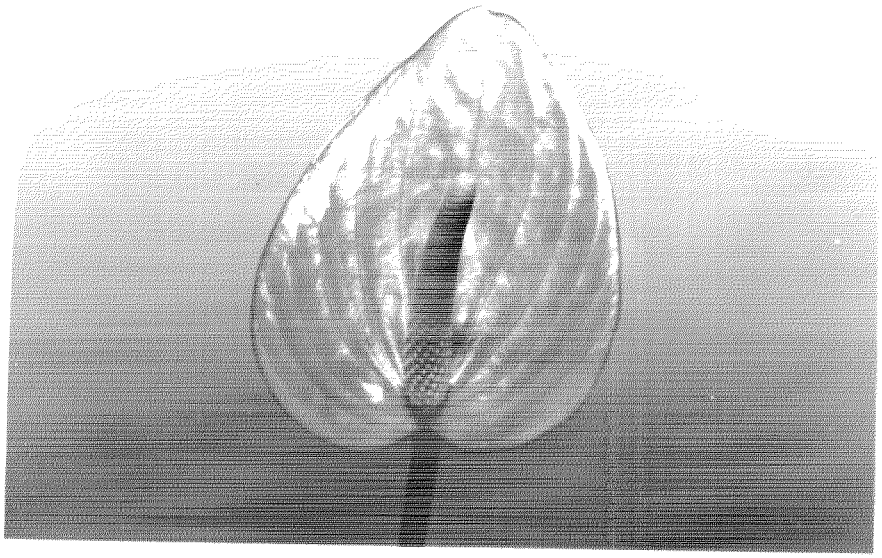
FIG. 2 illustrates the mature influorescence.
Figure 3:
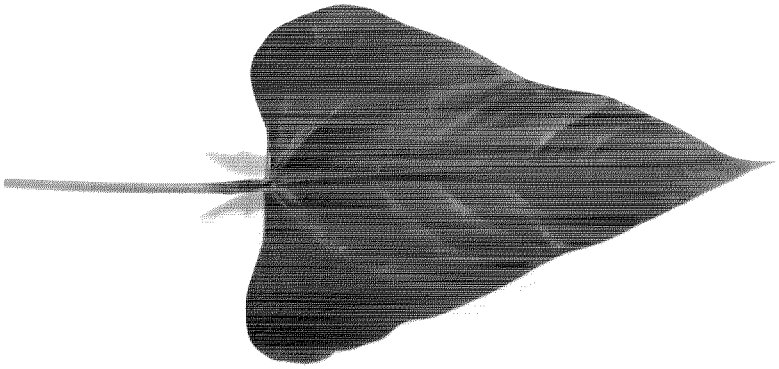
FIG. 3 illustrates a top of a mature leaf.
Figure 4:
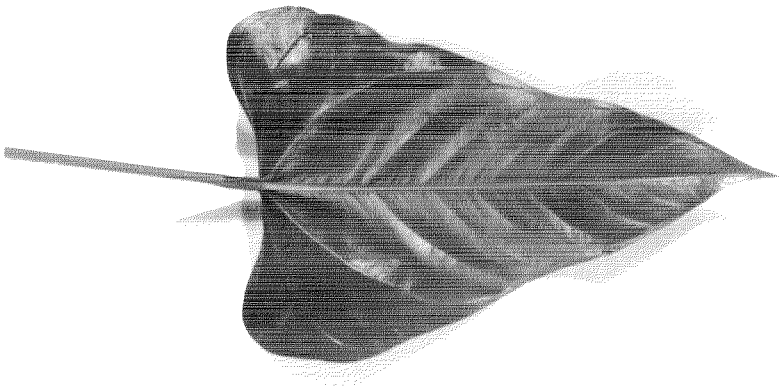
FIG. 4 illustrates the bottom of a mature leaf.

The following observations and measurements describe plants grown near Altha, Fla. under greenhouse conditions. These observations and measurements were recorded in March and April, 1996 from plants grown in 10 cm pots, about 10 months from planting tissue culture produced microcuttings. Older plants may be different in some morphological characteristics e.g., leaf and spathe shape. Fully developed organs were used for measurements and color description, unless otherwise indicated. Color values were determined Mar. 29 through Apr. 3, 1996 under natural, indirect light of approximately 200–290 foot-candles. Color references are made to The R.H.S. Colour Chart, except where general color terms of ordinary significance are used.

'A2' has not been observed under all possible environmental conditions. The phenotype may vary with variations in environment and horticultural practices, such as temperature, light intensity, day length, fertilization and propagation procedure, without any change in genotype.

Parentage:

*Female parent.*—Selected clone of Anthurium 'Julia' designated "J90302".

*Male parent.*—Selected *Anthurium andreanum* designated "AR891".

Propagation: Plant tissue culture.

Plant descriptions:

*Growth habit.*—Dwarf, with a short main stem, relatively open.

*Height.*—Foliage 12–20 cm; with spathes 16.5–21 cm.

*Width.*—26.5–30 cm.

Petiole:

*Size.*—6.8–8.1 cm long, 2.7–3.6 mm in diameter at the mid length.

*Geniculum.*—1.1–1.3 cm long, 3.4–4.3 mm in diameter at the base, inconspicuous.

*Petiole wings.*—1.3–1.7 cm long, inconspicuous.

*Color.*—Geniculum: Adaxial: Darker than 146A (yellow-green) with some greyed-orange (165A) tint. Abaxial: A mixture of one of the following yellow-green colors: 144A, 144B, 146B. Below geniculum: Adaxial: Similar to geniculum; the amount of greyed-orange decreases towards base; base close to 146A-B (yellow-green). Abaxial: Distal part darker than geniculum — approximately 146A or between 146A and 146B; base a little lighter — closer to 146B (yellow-green). Petiole wings: 146B (yellow-green).

Lead blade:

*Position.*—Midrib of most leaf blades approximates horizontal position or tip is slightly pointing upwards.

*Shape.*—Ovate, slightly asymmetric; tip acuminate, base truncate with cordate tendencies, sometimes slightly asymmetric. Bases tend towards truncate or obtuse during early plant development, but later — produced bases tend toward cordate. The lobes curve upward; this feature becomes progressively more pronounced as plant ages.

*Size.*—11.1–13.3 cm long; 6.6–8.6 cm wide; length to width ratio 1.5–1.7:1.

*Texture.*—Thick, leathery, smooth, slightly glossy; young leaves more glossy.

*Veins.*—Prominent near the base, less conspicuous near the tip.

*Color.*—Newly unrolled, not expanded leaf: Adaxial: Darker than 146A (yellow-green); area adjacent to petiole lighter (146A-B). Abaxial: Distal part similar to 148A (yellow-green), closer to the base with some 148B. Mature leaf: Adaxial: Darker than 147A (yellow-green); veins: proximal approximately ¼ of midrib and short sections of primary veins (up to 1–1.5 cm) 165A (greyed-orange); remaining parts of veins not distinct — a little lighter or the same color as surrounding tissue. Abaxial: Between 146A and 147B (both yellow-green); veins: midrib 146B-C (yellow-green); protruding parts of other primary veins slightly lighter than the surrounding tissue.

Scale leaf covering lateral vegetative bud (Mature, presenescent scale leaf described):

*Length.*—4.5–6.3 cm; rolled longitudinally, except for the base.

*Color.*—Abaxial: Midrib 144B (yellow-green) except for the tip, where it is 144A; areas on both sides of midrib 144B-C, slightly translucent.

Scale leaf between peduncle and the main stem:

*Length.*—1.9–2.5 cm.

Inflorescence:

*Arrangement.*—Spathes above foliage on straight, strong, thick, peduncles. Spadix low on the spathe. Ratio spathe length to spadix length is 1.3–1.8:1. Peduncle front side distance between spathe and the lowermost flowers on the spadix 5.0–6.5 mm.

*Development.*—As the bud starts unrolling above foliage it is approximately vertical or slightly lean backwards. Soon after spathe opens pistils start protruding at the base of spadix and spathe starts leaning away from spadix, which remains approximately vertical through senescence; at infloresence maturity proximal part of spathe's midrib forms aproximately 60°–90° angle with spadix; tip may be at various angles.

Peduncle:

*Size.*—10.5–14.4 cm long; 3.1–3.8 mm in diameter at the mid length.

*Stipe.*—Approximately 1–2 mm long.

*Color.*—Front: 144A-B above spathe, 146A-B, 144A (all yellow-green) below spathe. Back: 146A at the top, gradually merges with 144A (both yellow-green) at the base.

Spathe:

*Shape.*—Between deltoid and ovate; at maturity rarely cupped. Edges slightly roll frontwards. Tip — aristate, 2–3 mm long; base — cordate or between truncate and cordate, sometimes slightly asymmetric; lobes slightly extend past peduncle.

*Size (flattened).*—5.1–6.4 cm long, 4.8–6.7 cm wide; length to width ratio 1.0–1.2:1. Spathes produced by older plants are more ovate, with a greater length to width ratio, more often slightly cupped and usually slightly more upright at maturity.

*Texture.*—Smooth, leathery, slightly puckered, slight glossiness at maturity is less than when young.

*Color.*—Closed bud: 47A-B (red).

*Newly unrolled spathe (pistils emerging at the base).*—Front: 47A (red). Back: One or a combination of the following red colors: 47B, 48A 50B, 51A, 45D, 46D.

*Mature spathe (fully developed pistils on basal approximately ¾ of spadix).*—Front: 47B, 45D (both red). Back: Most similar to 48A, sometimes with some addition of 51B and/or 48B and/or 47D (all red).

Spadix:

*Shape.*—Columnar, slightly tapering in distal part.

*Size.*—3.4–4.0 cm long, 6.0–7.0 mm maximum diameter.

*Color.*—Young inflorescence: Proximal zone with pistils emerging, most similar to 36C-D, usually with some addition of 37D, 38D, 39D, 49C (all red); gradually merges with distal yellow-green (153B-C, 152D, 151A); tip 151B. Mature inflorescence: Proximal ¾ of spadix (with fully developed pistils) most similar to 29D (orange) with some addition of red (36B-C, 38D, 49D); distally the amount of red increases until it merges with a 5–7 mm zone of uneven color composed of the red colors: 49A, 47D, 48B, 50C 51B-C, 52C-D, 54B-C and 55B (in which pistils start protruding); above this zone a color darker than or similar to 34D or 31C (both orange-red) is intermixed with a color darker than 161A (greyed-yellow); towards tip proportion of greyed yellow to orange-red increases.

Botanical flower:

*Perianth.*—Well visible between pistils, segments united.

*Pistil.*—Small, similar in color to perianth; stigmas minute.

*Stamens.*—Not visible, no pollen produced.

Flowering: Flowers naturally in 10 cm pots, about 7–8 months from planting tissue cultured microcuttings. Continuous year-round flowering. Approximately 10 months after planting tissue cultured microcuttings two to three pink spathes present above or among leaves.

Spathe longevity: Spathe remains pink for approximately 9–10 weeks following appearance of bud above or among foliage and then gradually changes to a green color continuing to enhance ornamental value of a plant for several months past maturity. Seven months after appearance of buds green spathes with a little cream coloration were still present on the plant.

Roots: Roots developed above soil line are very thick, fleshy, non-branching; they are red when young, later brown. Roots developed below soil line are fleshy, branched with fine lateral roots,cream in color with yellow root caps.

Disease and insect resistance: No unusual susceptibility to diseases or insects noted to date.

Comparison with the Known Cultivars

The new cultivar can be compared to the known cultivar 'Ruth Morat' U.S. Plant Pat. No. 8,540 a/k/a/ Lady Ruth and to 'Julia'. The comparisons were made on plants grown under similar conditions in a greenhouse near Altha, Fla.

'A2' is distinguished from 'Ruth Morat' by its much smaller size; lesser branching; more upright growth habit and much earlier flowering. At the time of description 10 month old 'A2' plants had 2–3 good quality inflorescences (at least one unrolled spathe) whereas only a few of 'Ruth Morat' plants of approximately the same age had one small closed bud of poor quality. A saleable plant of 'A2' is achieved in at least ⅓ less time than is 'Ruth Morat'. Spathes of 'A2' are larger in proportion to foliage and plant size than spathes of 'Ruth Morat'.

'A2' is distinguished from 'Julia' by its much more vigorous growth; earlier and more abundant branching; earlier flowering; larger and ovate leaf blades; thicker and stronger peduncles; larger, longer-lasting, pink spathes and larger cream-pink spadixes. A saleable plant of 'A2' can be produced in about half the time required for 'Julia'.

I claim:

1. A new and distinct cultivar of Anthurium plant names 'A2', substantially as described and illustrated herein, characterized particularly as to novelty by its dwarf growth habit; vigorous growth; early branching; abundant, year-round and exceptionally early flowering; good quality inflorescence from the onset of flowering; exceptionally long-lasting, pink spathes, large in relation to the plant, held above foliage on straight, exceptionally thick and strong, peduncles and not turning brown after maturity.

* * * * *